United States Patent [19]

Ker et al.

[11] Patent Number: 5,090,817
[45] Date of Patent: Feb. 25, 1992

[54] POUR POINT DETECTION

[75] Inventors: Victoria S. Ker; Charles Tsang, both of Calgary, Canada

[73] Assignee: Nova Corporation of Alberta, Calgary, Alberta, Canada

[21] Appl. No.: 638,738

[22] Filed: Jan. 8, 1991

[30] Foreign Application Priority Data

Sep. 20, 1990 [CA] Canada .......................... 2025889-6

[51] Int. Cl.$^5$ .......................................... G01N 25/02
[52] U.S. Cl. ...................................... 374/24; 73/64.1; 374/16
[58] Field of Search ............... 374/16, 20, 24, 28; 73/64.1

[56] References Cited

U.S. PATENT DOCUMENTS

| 3,122,911 | 3/1964 | Conklin | 374/24 |
| 3,161,039 | 12/1964 | Kapff | 374/20 |
| 3,442,116 | 5/1969 | Brown | 374/24 |
| 3,491,582 | 1/1970 | Kleiss | 374/16 |
| 4,484,821 | 11/1984 | Willcock | 374/24 |
| 4,946,288 | 8/1990 | Siska et al. | 374/20 |

Primary Examiner—Daniel M. Yasich
Attorney, Agent, or Firm—Stevens, Davis, Miller & Mosher

[57] ABSTRACT

The present invention relates to an apparatus and process for estimating the pour point of a hydrocarbon oil. The pour point of hydrocarbon oil gives an indication of its low temperature properties, and is determined according to the time-consuming procedures set out in the American Society of Testing and Materials (ASTM) test D-97. The present invention generally provides a convenient means to estimate the pour point of a hydrocarbon oil, by directing a flow of pressurized gas towards a sample of the oil, and determining the warmest temperature at which the gas flow does not cause a substantial surface wave on the oil surface.

14 Claims, 4 Drawing Sheets

POUR POINT DETECTION

FIELD OF THE INVENTION

This invention relates to the measurement of the power point of a hydrocarbon oil. More specifically, the present invention provides an apparatus and method for estimating the pour point of a hydrocarbon oil.

BACKGROUND OF THE INVENTION

The pour point of a hydrocarbon oil is measured according to the procedures described in ASTM test D97.

ASTM test D97 is comparatively time consuming and cumbersome, so it would be clearly desirable to have a convenient process to estimate the pour point of an oil.

Thus, it is not surprising that many previous attempts have been made to provide a convenient process to measure the pour point of oil.

The following U.S. patents relate to methods to estimate pour point, but none of the methods has achieved universal acceptance:

U.S. Pat. No. 3,580,047 (Simpson); U.S. Pat. No. 3,646,802 (Nolting); U.S. Pat. No. 4,508,460 (Croo); U.S. Pat. No. 3,498,104 (van Kerkvoort); U.S. Pat. Nos. 3,201,970; 3,202,602; 3,590,627 (Beaugh); U.S. Pat. No. 4,700,562 (Altman et al); U.S. Pat. No. 3,077,764 (Kapff); U.S. Pat. No. 3,248,928 (Conklin); U.S. Pat. No. 3,413,836 (Nadeau); U.S. Pat. No. 3,491,582 (Kleiss); U.S. Pat. No. 3,496,760 (Puzniak); U.S. Pat. No. 3,442,116 (Brown); U.S. Pat. No. 3,122,912 (O'-Neill); and U.S. Pat. No. 3,161,039 (Kapff).

The inventions listed above have not received universal acceptance due to one or more perceived disadvantages, such as a lack of precision and/or accuracy in the test results; or due to the mechanical complexity of the machines required to complete the test. It is an object of the present invention to mitigate the disadvantages of the prior art attempts to estimate the pour point of oil.

SUMMARY OF THE INVENTION

In one embodiment, the present invention provides an apparatus for estimating the pour point of a hydrocarbon oil, said apparatus comprising:
 i) a receptacle adapted to receive a sample of said oil,
 ii) means for providing a flow of pressurized gas directed towards the top surface of said oil, wherein said flow is of sufficient strength to cause a significant surface disturbance on said oil when said oil is at a temperature of about 20° C., but of insufficient strength to splash the majority of said oil out of said receptacle,
 iii) means for changing the temperature of said oil,
 iv) monitoring means for monitoring said top surface of said oil, and
 v) temperature measuring means for measuring the temperature of said sample.

In a preferred embodiment, the monitoring means of the above defined apparatus comprise:
 a) a light beam source located to direct a beam of light towards the top surface of the oil sample at an incident angle so that the light beam is largely reflected or absorbed by the top surface, and
 b) scattered light detection means arranged so as to detect light scattered by the sample and changes in the intensity of the scattered light, wherein the detection means are connected into circuit means capable of registering change in light scattered from the sample.

The present invention also provides a process to estimate the pour point of a hydrocarbon oil by establishing the warmest temperature at which a suitable pressurized gas flow will not cause a significant disturbance on the surface of said oil, said process comprising:
 i) providing a sample of said oil in a receptacle,
 ii) subjecting the top surface of said sample to a flow of pressurized gas directed towards said top surface, wherein said flow is of sufficient strength to cause a surface disturbance when said oil is at a temperature of about 20° C., but of insufficient strength to splash the majority of said oil out of said receptacle,
 iii) changing the temperature of said oil,
 iv) monitoring said top surface of said oil, and
 v) measuring the warmest temperature at which said surface disturbance is substantially diminished.

The present invention relates to a process and apparatus for estimating the pour point of a hydrocarbon oil. The term hydrocarbon oil is not meant to place any undue restriction on the present invention, and includes all oily materials which are conventionally subjected to pour point tests. Examples of hydrocarbon oils are light distillates such as diesel; intermediate and heavy fuel oil, conventional lube oils, and lube oils containing additives such as detergent, viscosity index improvers and the like.

Through extensive experimentation, I have now confirmed that there is an excellent correlation between the ASTM pour point of a hydrocarbon oil and the (warmest) temperature at which a flow of pressurized gas will not cause a surface disturbance or the oil. This disturbance may be described as a surface wave or ripple. It has been observed that when hydrocarbon oil is cooled to a temperature below its pour point, a flow of pressurized gas over the surface of the oil will not cause a surface wave. Thus, in general, the process of the present invention is directed towards estimating the pour point of an oil by measuring the warmest temperature at which a gas flow will not cause a surface wave in the oil (or alternatively stated, the coolest temperature at which a gas flow will cause a surface wave in the oil).

The present process is not meant to be restricted to the use of any particular type of gas flow. For convenience, it is desirable to utilize a readily available source of dry bottled gas, such as nitrogen or air, delivered in a conventional gas cylinder.

The gas flow must have sufficient "strength" to disturb the top surface of the oil at room temperature.

The term "strength" as used herein with reference to gas flow, is meant to describe a combination of pressure and flow rate. Simply stated, the gas flow must have sufficient strength to disturb the surface of the oil at room temperature (i.e. at or about 20° C.). A suitable gas flow strength can be readily established by directing the gas flow at the surface of the oil sample at room temperature and adjusting the strength until a wave or ripple is visually observable. A gas flow strength which is established in this manner is suitable for use in the entire process of the invention.

It will also be apparent that the strength of the gas flow must not be too high to splash most of the sample out of the receptacle.

As a general guideline, the effective strength of the gas flow will be dependent upon both of the distance between the gas source and the sample and the angle at which the gas flow is directed towards the oil.

In practice, the use of bottled dry air at a pressure between 0.5 and 10 pounds per square inch (preferable from 1 to 5 psi) has been found to be suitable for use in the present invention when directed towards the surface of the oil from a small diameter nozzle located less than 10 cm from the oil surface.

As previously noted, the flow of pressurized gas causes a small surface wave on the oil.

For convenience of monitoring this surface wave, it is preferred that the flow of pressurized gas be provided in distinct pulses, so as to provide discrete waves in response.

The process of the present invention may be undertaken using one of two alternative modes with respect to the manner in which the temperature is altered, namely:

i) the oil sample may originally be at a temperature higher than its pour point, then cooled to a temperature below its pour point, or ii) conversely, the oil sample may originally be at a temperature below its pour point (as a result of being pre-cooled by, for example, being placed in a freezer), with the present process then being completed by warming the oil to a temperature higher than its pour point The first mode is normally the easiest. For example, the process of this invention can be undertaken using an oil sample which is originally at room temperature, then cooling the sample to below its pour point. Certain heavy oils have relatively high pour points (e.g. 12°–15 °C.). It is preferred that such heavy oils be heated prior to estimating their pour point (as directed by ASTM procedure D-97).

The use of a controlled cooling rate helps to ensure the accuracy of the process. A cooling rate of between 0.3° and 5° C. per minute gives good results, with a rate between 0.6° and 2.0° C. per minute being preferred. Slower rates are generally inconvenient, and higher rates can cause the formation of temperature gradients which adversely affect the process.

The accuracy of the pour point estimates obtained by the present invention is partially dependent upon achieving a uniform temperature throughout the sample of oil being tested. The receptacle for containing the oil sample can be constructed to help achieve this desired accuracy.

In particular, the sample receptacle preferably has the following characteristics:

i) a small total volume (to reduce the thermal mass of the sample)
ii) a generally flat bottom surface which is manufactured from a material having a high heat conductivity;
iii) a shallow sample containment area (i.e. such that the oil sample is contained as a thin layer), and
iv) "splash guard" walls which are substantially higher than the depth of the oil sample It is especially desirable to use an oil sample having a volume of less than 0.5 cubic centimeters (c.c.), and a depth of less than 2 m.m.

A receptacle with walls having a height of 6.5 to 10 m.m. generally provides adequate control against splashing of a sample of this size.

It is essential that the temperature of the oil sample is monitored. Conventional temperature monitoring means, such as a thermometer or thermocouple, are suitable for this purpose.

In order to establish the temperature at which a gas flow does not cause a surface wave, means to monitor the oil surface must be provided.

This may be done "manually" (e.g. by simply observing the test) or by automated mechanical, or automated electro-mechanical means.

It is preferred that the monitoring be completed on an automated basis. An example of an automated monitoring means employs a combination of:

i) a light beam directed at the surface of the oil sample,
ii) means to monitor the reflected or scattered light from the sample, and
iii) means to detect a difference in the intensity of the scattered and/or reflected light.

Further details and features of the present invention will be apparent from a consideration of the accompanying drawings, which illustrate a preferred, non-limiting embodiment of an apparatus according to the invention.

BRIEF DESCRIPTION OF THE DRAWINGS

The invention will be described in more detail with references to the accompanying drawings, which show a preferred embodiment of the apparatus and in which.

DESCRIPTION OF THE PREFERRED EMBODIMENT

Figure 1:
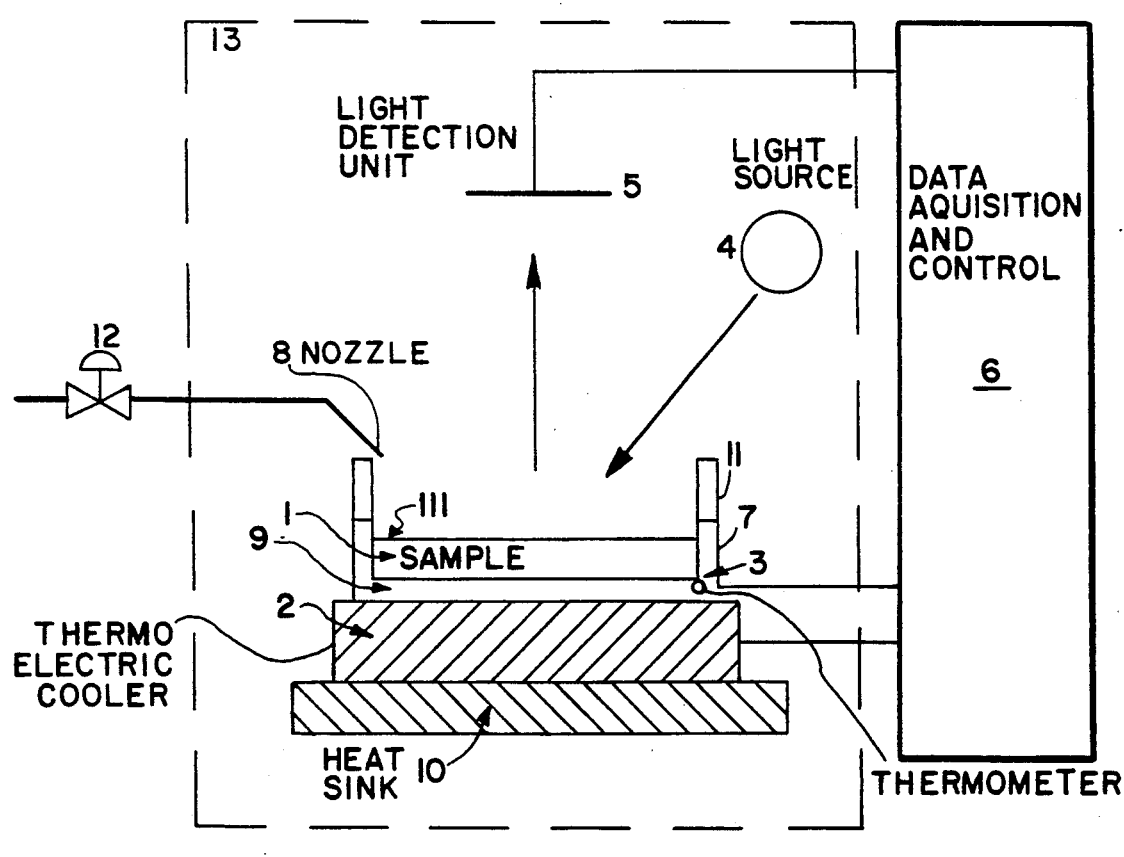
FIG. 1 is a schematic drawing of an apparatus according to the present invention.

The apparatus for estimating the pour point of oil which is illustrated in FIG. 1 consists of a light proof chamber 13, a light source 4, a light detection unit 5, a non-light scattering surface 9 which forms the bottom of a receptacle 7 for liquid sample 1, a thermoelectric cooler 2 in thermal contact with the surface 9 of the receptacle and a heat sink 10, a nozzle 8 located in close proximity to the top surface 111 of the oil, a solenoid valve 12, a splash guard 11, a thermometer 3, and a data acquisition and control unit 6. The data acquisition and control unit 6 is used to collect information from the thermocouple 3 and the light detection unit 5, to control the cooling rate of the surface 9, to control the opening of the solenoid valve 12 at appropriate temperature intervals, and also to analyze the collected data. A computer equipped with the necessary software and hardware is utilized for this purpose. The thermoelectric cooler can be used for both cooling and heating.

Figure 2:
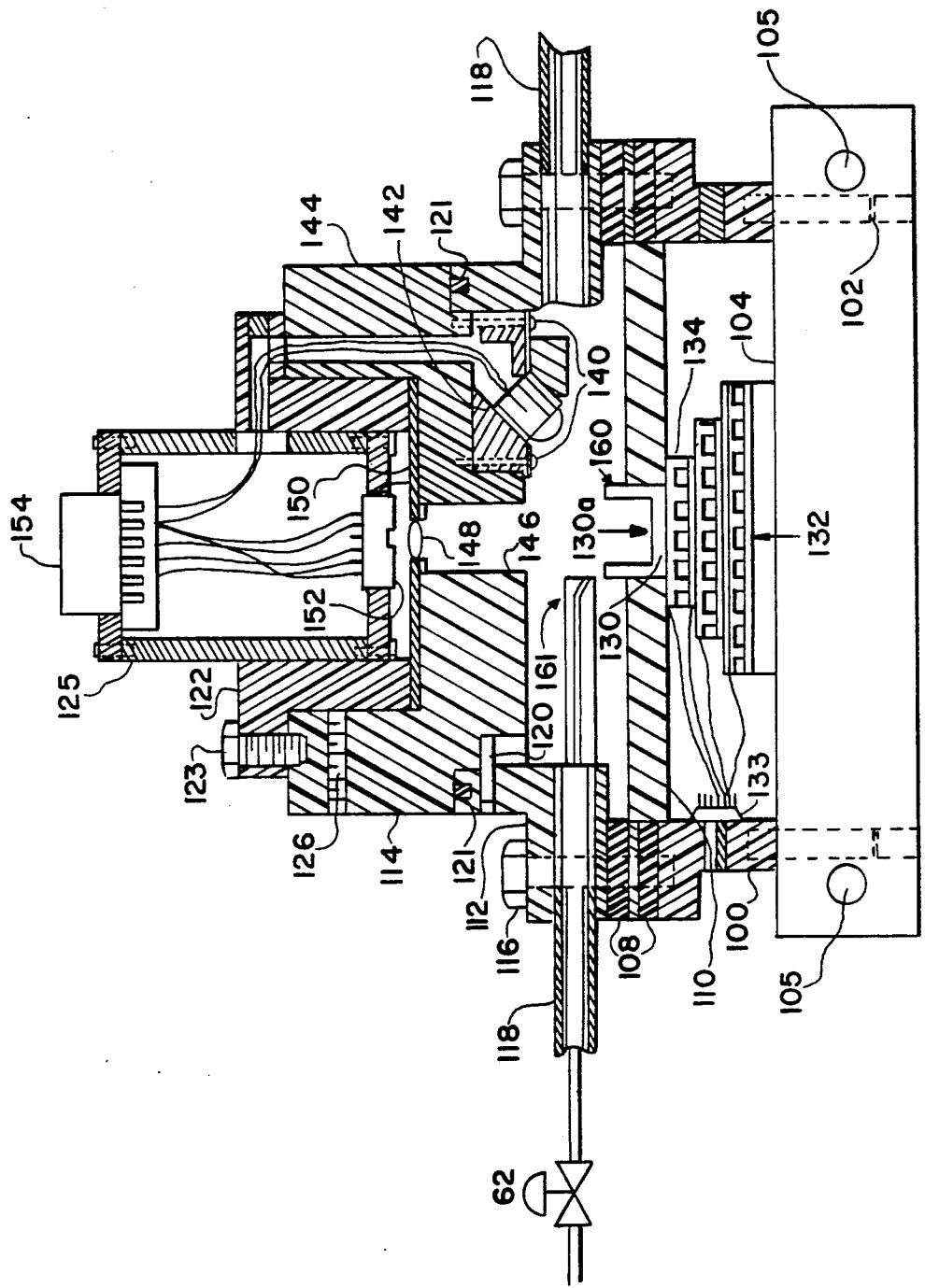
FIG. 2 is a sectional elevation through an apparatus according to the present invention.

FIG. 2 provides a more detailed illustration of a preferred apparatus. The chamber is designed to withstand a gas pressure of approximately 5–10 psig. As shown, an annular base part 100 is mounted by bolts 102 onto a water cooled, metallic heat sink 104 having water ducts 105. The base part supports, via gaskets 108, the horizontal bottom 110 of a light excluding chamber having an annular housing 112 with a large central aperture normally closed by a readily removable top part 114. The housing 112 is fixed to bottom 110 and base 100 by bolts 116. It has radial ducts connected to gas inlet and outlet tubes 118 so that the chamber can be purged with a non-condensing gas. This is to reduce condensation of water vapour inside the chamber as the chamber is cooled during a pour point measurement.

The top part 114 is removable secured to housing 112 by a bayonet type coupling, i.e. the kind of two component having radial pins on one component which engage in partially circumferential grooves in another component. Here, the coupling includes radial pins 120 which project inwardly from housing 112 and engage in grooves in the adjacent cylindrical surface of top part 114, the grooves having axial portions allowing entry of the pins and circumferential portions allowing locking. An 0-ring 121 provides a seal between the two parts.

The parts 110, 112,114 and 122 are all made of black plastic material, so as to be light absorbing and so as to be thermally insulating at least as compared to metal parts. Nylon or ABS plastic may be used.

The center of the bottom 110 has a circular aperture at the bottom which is counterbored to receive a receptacle 130 formed from copper; this fits snugly within the counterbore so that the upper walls of the aperture are continuations of the inner walls of the receptacle. The walls 160 of the receptacle form a splash guard and reduce splashing of the sample when a pulse of pressurized gas is emitted. The receptacle walls 160 should be about 6.5 mm to 10 mm in height above the upper surface 130a, and the height: diameter ratio of the well formed by the receptacle and side walls is about 1:1.5. In this preferred embodiment, the upper surface 130a is a highly polished flat mirror, and the amount of oil which is placed in the receptacle during the process of the present invention is less than 0.5 c.c., especially less than about 0.2 c.c.

The nozzle 161 attached to the wall of the chamber and positioned opposite the light source 144 is used for sending a pulse of pressurized dry gas to the surface of the liquid sample at appropriate intervals. The nozzle 161 is positioned at an approximately 90° angle to the light source (when considered in a plan view). The strength of the gas pulse is dependant upon the pressure of the compressed gas, the orifice diameter of the nozzle and the distance between the nozzle and the sample surface. The nozzle is positioned close to the liquid surface but far enough away that the nozzle will not be adversely wetted by splashing. A distance of about 0.3 to 2.0 cm and is generally satisfactory. A preferred nozzle diameter for the apparatus shown in FIG. 2 is approximately 0.3 cm. A nozzle of this diameter can be conveniently fabricated from ⅛" (outside diameter) metal tubing. The solenoid valve 162 located upstream of the nozzle is normally blocked The valve 162 is opened at regular temperature intervals for a short time to provide a distinct pulse of pressurized gas, directed at the liquid surface.

Between the lower side of the receptacle 130 and the heat sink 104 is firmly held a thermoelectric cooler 132 which is in good heat conductive contact with both the receptacle and the heat sink. The receptacle and heat sink are preferably constructed from conductive metal. The cooler is capable of reducing the temperature of the receptacle to −50 degrees C. or lower.

The cooler 132 is spaced well away from the walls of the base 100. The base is provided with a side bore holding a connector 133 for wires which run both to the cooler 132 and to a platinum resistance thermometer 134. The thermometer is affixed to the bottom of the receptacle 130 and is also in good thermal contact with the mirrored surface 130a.

A shallow cylindrical recess in the top part 114 holds, by screws 140, a light holder 142 which mounts a light emitting diode 144. This is arranged to direct a beam of light onto the mirror surface 130a, at an angle between 20 to 70 degrees, preferably 45 degrees. (where the angle is measured as the acute angle between the light beam and the horizontal surface of the oil).

Co-axially above the receptacle 130 is a bore 146 in part 114. This bore is of similar diameter to the receptacle and terminates just short of the lower surface of the recess which receives bushing 122. A light detection device 152, used to detect a change in the reflected light pathway caused by surface movement of the oil, is placed directly above the mirrored surface 130a so as to be on a light transmittance path to the mirrored surface. The detection device 152 consists of an array of charged coupled devices (CCD) having a plurality of light detectors, and is mounted on a rod 125. The CCD preferably has one hundred an twenty eight pixels of light detectors. The rod 125 is movable in the vertical direction and thus allows for adjustment of the CCD, to optimize the reception of the reflected light beam through a fixed lens 148. The fixed convex lens 148 has its edges held between the periphery of the central aperture 146 and the periphery of a similar aperture in a metal plate 150 held between part 114 and bushing 122. The lens 148 focuses light received from the mirrored surface 130a onto the CCD thus making this arrangement extremely sensitive to small amounts of light. In addition, the multi-pixel light detector provides much greater light sensitivity compared to a single cell light detector. Each pixel of the CCD array is connected via connector 154 to a data acquisition and control unit which monitors sequentially each of the pixels of the CCD array and also controls the scanning rate. The leads from the light emitting diode 144 also pas through the same connector.

The method of operation, when used for detecting pour point in a liquid, will now be described with reference to FIG. 2. Prior to the test, one must ensure that the mirror 130a is clean and dry. The top of the chamber 114 is opened, and liquid sample is introduced into the chamber using a pipette or dropper to place about 0.1-0.2 mls of liquid onto the mirror 130a, followed by closing the top. The chamber is then purged slowly with a dried gas; this purge stream is preferably left on throughout the entire run. The temperature of the mirror is lowered by a thermoelectric cooler 132 at a predetermined rate (most preferably, about 0.8 deg c/min.) which is controlled by the data acquisition and control unit. The light source 144 is then activated and the light beam is directed onto the mirror 130a. At regular temperature intervals (normally 1° to 3° C. intervals), the control unit opens the solenoid valve 162 to turn the valve on for a short time period (about 100 to 200 milliseconds). This provides a distinct pulse of pressurized gas emitting from nozzle 160, directed towards the sample surface. At temperatures above the pour point of the oil, the surface is moved by the pulse of gas. The movement becomes negligibly small when the pour point is reached. Surface movement of the sample is detected by the light detector 152 and is indicated by a substantial increase in the reflected light received by the CCD 152. A computer is used for data acquisition and control; control of the cooling of the mirror surface 130a and the pulse rate of the pressurized gas; and for processing signals received from the thermometer 134 and the CCD array 152. The processed signals are then displayed on a monitor screen.

Figure 3:
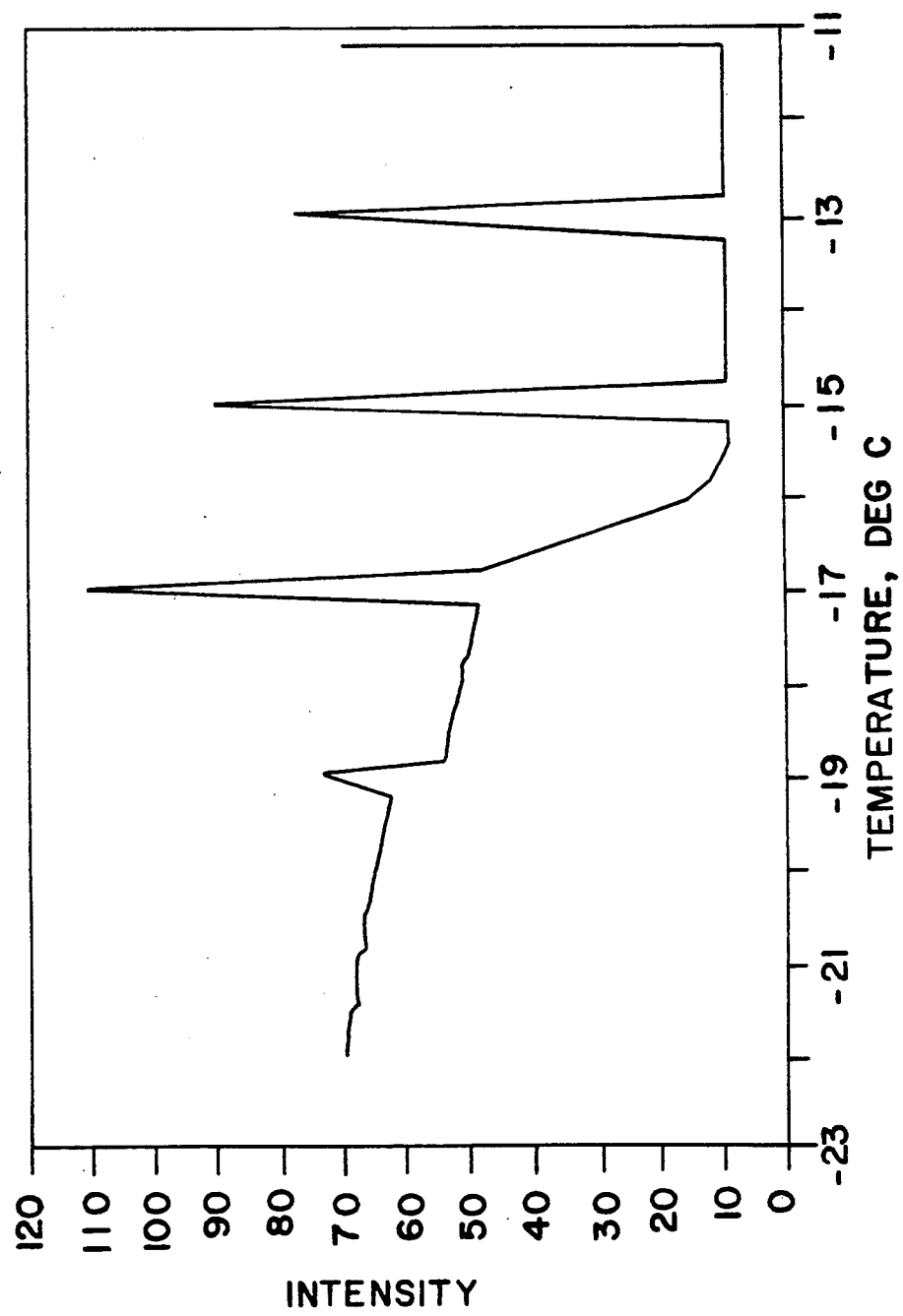
FIG. 3 is a graph of experimental results obtained by using an apparatus according to the present invention to estimate the pour point of a diesel oil.

FIG. 3 illustrates data obtained by employing the present invention to estimate the pour point of a diesel fuel. Details of this experiment are described below.

A sample of about 0.2 cc of the diesel fuel was placed in the receptacle of the apparatus illustrated in FIG. 2. The apparatus chamber was then closed, and the test was initiated. A light beam from the light emitting diode (144 in FIG. 2) was directed towards the sample, and the sample was cooled by the thermoelectric cooler at a rate of about 0.8° C./min. Dry purge air was provided at a very low flow rate to reduce condensation problems (note: this purge air flow does not have sufficient strength to disturb the surface of the sample). Pressurized air was pulsed through a nozzle located in close proximity to the sample surface at temperature intervals of about 2° C. (i.e. at time intervals of about 2.5 minutes). Prior to each air pulse, the light beam is almost entirely reflected away from the light detector, and only a small quantity of light is detected b the detector (this is shown by the generally smooth line in FIG. 3). After an air pulse is emitted (at temperature above the pour point), the sample surface is disturbed and the intensity of light on the detector increases substantially. The light intensity decreases once this surface motion ceases, resulting in a "spike" on the light intensity level graph. Such "spikes" are clearly evident at temperatures of $-11°$, $-13°$, $-15°$, $-17°$ and $-19°$ C. (and are a result of the gas pulses at those temperatures). However, as illustrated in FIG. 3, no "spike" was observed at temperatures below $-19°$ C. Accordingly, the pour point of this diesel fuel is estimated at $-19°$ C. from the experimental results shown in FIG. 3 as the data suggest that this is (approximately) the warmest temperature at which the gas flow will not cause a surface wave (note: the accuracy of measuring the warmest temperature at which a disturbance is observed might be improved, if desired, by employing a slower rate of temperature change and/or more frequency air pulses).

Thus, by monitoring the surface of the sample using a light intensity detector, the pour point of a hydrocarbon oil can be conveniently estimated.

At the end of a pour point process measurement, the thermoelectric cooler is switched off to allow the apparatus to warm up to the ambient. The purge gas is then switched off, and the chamber is opened to allow cleaning of the sample receptacle.

Figure 4:
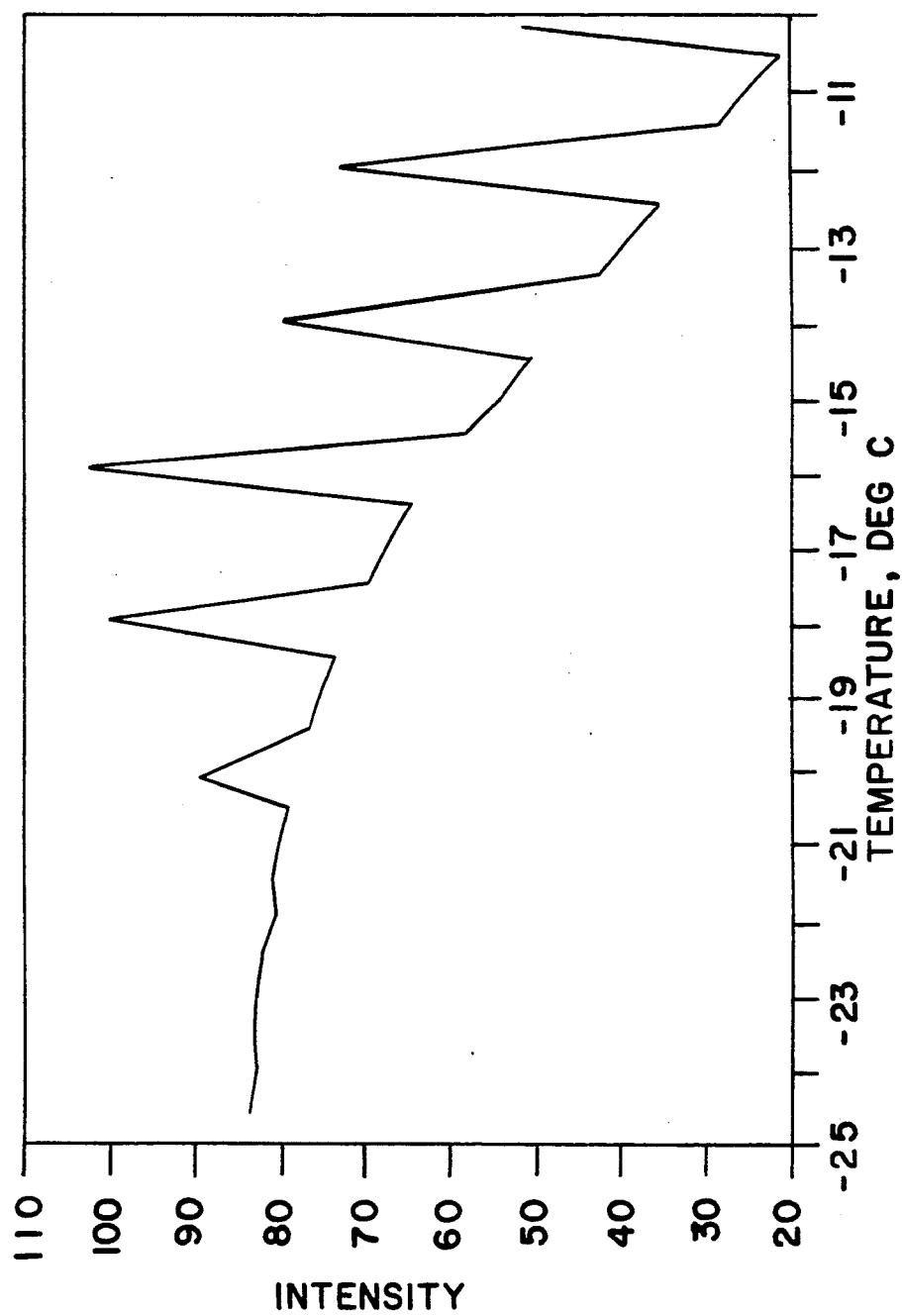
FIG. 4 is a graph of experimental results obtained by using an apparatus according to the present invention to estimate the pour point of a lubricating oil.

FIG. 4 illustrates data relating to the pour point of a lubricating oil. The data were again obtained using an apparatus of the type shown in FIG. 2, and using the experimental procedures as described above.

As is evident from FIG. 4, the pour point of the lube oil is estimated $-20°$ C.

EXAMPLE

This example provides data relating to the pour point of 14 commercially available lube oils.

The data were obtained:
i) by conducting pour point tests (according to ASTM D97), and
ii) by employing the present invention The "ASTM" and inventive experiments were conducted in duplicate or triplicate (as shown in Table 1).

The ASTM data were generated by up to three different operators (denoted operators A, B and C). Accordingly, the data shown in Table 1 give an indication of the operator-to-operator error associated with the ASTM procedures.

The inventive data were obtained using the experimental procedures described above (i.e. with respect to the description of FIG. 3) and the apparatus illustrated in FIG. 2.

The data shown in Table 1 clearly indicate that the averages of the pour point estimates obtained through the use of the present invention are in good agreement with the ASTM pour point averages.

Lube Oil Pour Point Data

| Exp. | Lube Oil Type | Estimated Pour Point (°C.) Inventive | ASTM Pour Point (°C.) (Technician Indicated in Brackets) |
|---|---|---|---|
| 1. | (E) 10W30 | −27 | −27 (A) |
|  |  | −27 | −27 (B) |
|  | (average) | −27 | −27 |
| 2. | (H) 10W30 | −25 | −27 (A) |
|  |  | −25 | −24 (B) |
|  | (average) | −25 | −24 |
| 3. | (V) 10W30 | −25 | −24 (A) |
|  |  | −25 | −24 (B) |
|  | (average) | −25 | −24 |
| 4. | (T) 10W30 | −27 | −27 (A) |
|  |  | −23 | −24 (B) |
|  |  | −25 |  |
|  | (average) | −25 | −26 |
| 5. | (S) 10W30 | −27 | −27 (A) |
|  |  | −27 | −27 (B) |
|  | (average) | −27 | −27 |
| 6. | (E) 10W40 | −23 | −24 (A) |
|  |  | −24 | −27 (B) |
|  | (average) | −24 | −26 |
| 7. | (S) 10W40 | −24 | −24 (A) |
|  |  | −24 | −27 (B) |
|  |  |  | −24 (C) |
|  | (average) | −24 | −25 |
| 8. | (T) 10W40 | −22 | −24 (A) |
|  |  | −22 | −21 (B) |
|  | (average) | −22 | −23 |
| 9. | (H) 15W40 | −20 | −24 (A) |
|  |  | −21 | −21 (B) |
|  | (average) | −21 | −23 |
| 10. | (E) 5W30 | −33 | −33 (A) |
|  |  | −39 | −33 (B) |
|  |  | −35 | −30 (C) |
|  | (average) | −36 | −32 |
| 11. | (S) 5W30 | −29 | −33 (A) |
|  |  | −29 | −30 (B) |
|  |  | −29 | −24 (C) |
|  | (average) | −29 | −28 |
| 12. | (M) 5W30 | −25 | −28 (A) |
|  |  | −27 | −30 (B) |
|  |  | −27 |  |
|  | (average) | −26 | −29 |
| 13. | (T) 5W30 | −31 | −33 (A) |
|  |  | −31 | −33 (B) |
|  |  | −31 |  |
|  | (average) | −31 | −33 |
| 14. | (M) 20W5 | −20 | −21 (A) |
|  |  | −20 | −15 (B) |
|  |  | −18 | −18 (C) |
|  | (average) | −20 | −18 |

Notes: All of the above data relate to commercially available lube oils. In the "Lube Oil Type" column, the bracketed letter indicates the supplier, and the remaining alphanumeric code - such as "10W30" in Experiment 1 - refers to conventional viscosity designations.

What is claimed is:
1. An apparatus for estimating the pour point of a hydrocarbon oil, said apparatus comprising:

(i) a receptacle adapted to receive a sample of said hydrocarbon oil, such that said sample of said hydrocarbon oil has a top surface;

(ii) means for providing a flow of pressurized gas directed towards said top surface of said sample of said hydrocarbon oil, wherein said flow is of sufficient strength to cause a significant surface disturbance on said sample of said hydrocarbon oil when said sample of said hydrocarbon oil is at a temperature of about 20° C., but of insufficient strength to splash the majority of said sample of said hydrocarbon oil out of said receptacle, (iii) means for changing the temperature of said sample of said hydrocarbon oil;

(iv) optical monitor means for monitoring movement of said top surface of said sample of said hydrocarbon oil; and (v) temperature measuring means for measuring the temperature of said sample of said hydrocarbon oil, said optical monitor means comprising:

(a) a light beam source located to direct a beam of light towards said top surface at an incident angle so that the light from the beam is largely reflected or absorbed by said top surface; and (b) scattered light detection means arranged so as to detect light scattered by said sample and changes in the intensity of the scattered light, wherein said detection means are connected into circuit means capable of registering change in light scattered from said sample.

2. The apparatus of claim 1 including a data processing and control means to control changing the temperature.

3. The apparatus according to claim 1 wherein said light detection means include a lens which focuses the light from said sample onto a light detecting element.

4. The apparatus according to claim 1 wherein said receptacle has a flat bottom surface and is formed from a heat conductive material.

5. The apparatus according to claim 4 wherein said means for changing the temperature consist of cooling means in thermal contact with said flat bottom surface and wherein said temperature measuring means are in thermal contact with said flat bottom surface.

6. The apparatus according to claim 1 wherein said receptacle is contained within a substantially light proof chamber having light absorbing internal surfaces, a gas inlet, a gas outlet and means for allowing ready access to the chamber for placing said sample in said receptacle.

7. The apparatus according to claim 6 wherein said scattered light detection means include a lens which focuses the light from said sample onto a light detecting element, and wherein said light beam is provided from a light emitting diode.

8. The apparatus according to claim 6 wherein said chamber contains a second gas inlet and a second gas outlet and wherein a non-condensing second gas flow is provided to said chamber to reduce the condensation of chilled vapor within said chamber.

9. A process to estimate the pour point of a hydrocarbon oil said process comprising:

(i) providing a sample of said hydrocarbon oil in a receptacle, such that said sample of said hydrocarbon oil has a top surface, (ii) subjecting said top surface of said sample of said hydrocarbon oil to a flow of pressurized gas directed towards said top surface, wherein said flow of pressurized gas is of sufficient strength to cause a significance surface disturbance when said sample of said hydrocarbon oil is at a temperature of about 20° C., but of insufficient strength to splash the majority of said sample of said hydrocarbon oil out of said receptacle, (iii) varying the temperature of said sample of said hydrocarbon oil;

(iv) monitoring said surface disturbance with optical monitor means as the temperature of said sample of said hydrocarbon oil is varied, wherein said optical monitoring comprises:

(a) directing a beam of light towards said top surface at an incident angle so that the light from the beam is largely reflected or absorbed by said top surface; and (b) detecting light scattered by said sample and changes in the intensity of the scattered light, and registering change in light scattered from said sample.

10. The process of claim 9 wherein said scattered light detection means include a lens which focuses the light from said sample onto a light detecting element.

11. The process of claim 10 wherein said light beam is provided by a light emitting diode and wherein said light detecting element consists of an array of light detecting elements.

12. The process of claim 9 wherein said flow of pressurized gas is provided as intermittent pulses.

13. The process of claim 12 wherein said pressurized gas is dry air having a pressure of between 0.5 and 5 pounds per square inch gauge.

14. The process of claim 9 wherein said sample is initially at ambient temperature, and is subsequently cooled at a rate of between 0.5° and 5° C. per minute.

* * * * *